(12) United States Patent
Hessler

(10) Patent No.: US 9,327,071 B2
(45) Date of Patent: May 3, 2016

(54) IMPLANTABLE FLUID DELIVERY SYSTEM WITH FLOATING MASS TRANSDUCER DRIVEN PUMP

(71) Applicant: MED-EL Elektromedizinische Geraete GmbH, Innsbruck (AT)

(72) Inventor: Roland Hessler, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 295 days.

(21) Appl. No.: 13/937,448

(22) Filed: Jul. 9, 2013

(65) Prior Publication Data

US 2014/0018736 A1   Jan. 16, 2014

Related U.S. Application Data

(60) Provisional application No. 61/671,263, filed on Jul. 13, 2012.

(51) Int. Cl.
| | | |
|---|---|---|
| *A61M 1/00* | (2006.01) | |
| *A61M 5/142* | (2006.01) | |
| *A61N 1/36* | (2006.01) | |
| *A61N 1/05* | (2006.01) | |

(52) U.S. Cl.
CPC .......... *A61M 5/14276* (2013.01); *A61N 1/0541* (2013.01); *A61N 1/36032* (2013.01); *A61M 5/1422* (2013.01); *A61M 5/14224* (2013.01); *A61M 2210/0662* (2013.01)

(58) Field of Classification Search
CPC ............... A61M 2210/0662; A61M 5/1422; A61M 5/14224; A61M 5/14276; A61M 2210/0668; A61M 2210/0675; A61M 5/142; A61M 5/14212; A61M 5/14216; A61M 5/14244; A61N 1/0541; A61N 1/36032; A61N 1/04; A61N 1/05; A61N 1/0526; A61N 1/18; A61N 1/32; A61N 1/36
USPC ......................................................... 604/151
See application file for complete search history.

(56) References Cited

U.S. PATENT DOCUMENTS

| | | | |
|---|---|---|---|
| 6,024,717 A | 2/2000 | Ball et al. | |
| 2003/0097121 A1* | 5/2003 | Jolly et al. | ................. 604/891.1 |
| 2008/0009836 A1 | 1/2008 | Fiering et al. | |

FOREIGN PATENT DOCUMENTS

| | | |
|---|---|---|
| WO | 03034960 A1 | 5/2003 |
| WO | 2012022920 A1 | 2/2012 |

OTHER PUBLICATIONS

International Searching Authority, International Search Report, International Application No. PCT/US2013/049650, dated Oct. 21, 2013, together with the Written Opinion of the International Searching Authority, 9 pages.

*Primary Examiner* — Jason Flick
(74) *Attorney, Agent, or Firm* — Sunstein Kann Murphy & Timbers LLP

(57) ABSTRACT

An implantable fluid delivery system for use in hearing systems includes an implantable fluid pump having a fluid chamber having at least one wall with a membrane, an inlet and an outlet in fluid communication with the fluid chamber, and a floating mass transducer coupled to the membrane. The membrane is configured to move in a first direction increasing a volume of the fluid chamber and to move in a second direction decreasing the volume of the fluid chamber, and the floating mass transducer is configured to cause the membrane to move in the first and second directions. The system further includes an implantable hearing device having one or more fluid channels in fluid communication with the fluid pump.

15 Claims, 8 Drawing Sheets

IMPLANTABLE FLUID DELIVERY SYSTEM WITH FLOATING MASS TRANSDUCER DRIVEN PUMP

CROSS REFERENCE TO RELATED APPLICATIONS

The present application claims priority to U.S. Provisional Patent Application No. 61/671,263 filed Jul. 13, 2012, the disclosure of which is incorporated by reference herein in its entirety.

TECHNICAL FIELD

The present invention generally relates to fluid delivery systems and, more particularly, the invention relates to implantable fluid delivery systems for use in hearing systems.

BACKGROUND ART

For many patients with hearing impairment, there are several types of implantable hearing devices, such as middle and inner ear implants, that can restore a sense of partial or full hearing. For example, cochlear implants can restore some sense of hearing by direct electrical stimulation of the neural tissue of the cochlea. The cochlear implant typically includes an electrode carrier having an electrode lead and an electrode array, which is threaded into the cochlea. The electrode array usually includes multiple electrodes on its surface that electrically stimulate auditory nerve tissue with small currents delivered by the electrodes distributed along the electrode array. These electrodes are typically located toward the end of the electrode carrier and are in electrical communication with an electronics module that produces an electrical stimulation signal for the implanted electrodes to stimulate the cochlea. In another example, a conventional hearing aid may be used to provide acoustic stimulation to the auditory system in the form of amplified sound when the impairment is related to the operation of the middle ear. In addition, groups of auditory nerve axons may be stimulated with electrodes placed within the modiolus, or auditory structures in the brain may be stimulated with electrodes placed on or within the structures, for example, on or within the cochlear nucleus.

With many implantable hearing devices, it is desirable to be able to deliver fluids, such as a drug solution, locally with the hearing device in order to treat disorders effectively or to prevent diseases, inflammation or apoptosis after implantation of the hearing device or even restore hearing (e.g., stem cells, nerve growth factors). Therefore, long term or intermittent fluid delivery capability is desired in these types of devices. Extremely low flow rates, however, are required for very small compartments, such as the inner ear with a total volume of about 70 µl, or a part of the inner ear, such as the scala tympani with a volume of about 30 µl. Currently, available pumps which are implantable are generally designed for implantation into much larger compartments, such as the abdominal region of the human body. Fluid delivery rates that are suitable for delivery into larger fluid spaces such as the circulation system (e.g., which consist of about 5-7 l of blood on average) or intrathecal (e.g., into the cerebrospinal fluid, which typically consists of more than 100 ml) are not suitable for smaller spaces. In small compartments, the fluid delivery should take place at flow rates that cause no substantial pressure increase, or only minimal increased pressure, within the compartment. Pumps with lower flow rates, however, are typically not suitable for implantation.

SUMMARY OF EMBODIMENTS

In accordance with one embodiment of the invention, an implantable fluid delivery system includes an implantable fluid pump having a fluid chamber having at least one wall with a membrane, an inlet and an outlet in fluid communication with the fluid chamber, and a floating mass transducer coupled to the membrane. The membrane is configured to move in a first direction increasing a volume of the fluid chamber and to move in a second direction decreasing the volume of the fluid chamber and the floating mass transducer is configured to cause the membrane to move in the first and second directions. The system further includes an implantable hearing device having one or more fluid channels in fluid communication with the fluid pump.

In some embodiments, the implantable hearing device may include a cochlear implant. The cochlear implant may include an electrode array having at least one stimulation electrode and at least one fluid outlet in fluid communication with the one or more fluid channels. The fluid delivery system may further include one or more reservoirs in fluid communication with the fluid pump. The reservoirs may be implantable and coupled to the fluid pump and/or external to the system and coupled to the fluid pump with a fluid connecting system. The fluid delivery system may further include a connecting member that couples the floating mass transducer to the membrane. The floating mass transducer may be disposed within the fluid chamber. The fluid chamber may include two chambers separated by the membrane. In the dual chamber configuration, the membrane is configured to move in one direction increasing the volume of one fluid chamber while decreasing the volume of the other fluid chamber, and configured to move in an opposing direction decreasing the volume of one fluid chamber while increasing the volume of the other fluid chamber. The fluid delivery system may include two reservoirs. The first reservoir may be in fluid communication with the first chamber and the second reservoir may be in fluid communication with the second chamber. When the dual chamber configuration is used, the implantable hearing device may have one or more fluid channels in fluid communication with one fluid chamber and one or more fluid channels in fluid communication with the other fluid chamber. In the dual chamber configuration, a portion of the floating mass transducer may be disposed in each of the two chambers or the floating mass transducer may be disposed within only one of the chambers. The inlets and the outlets may be on the same wall or may be on opposing walls.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Various embodiments of the present invention provide an implantable fluid delivery system for use in hearing systems. The delivery system includes an implantable membrane pump driven by a floating mass transducer and a hearing device coupled to the implantable membrane pump. The hearing device may include a middle ear and/or inner ear implant. The implantable membrane pump may be a single or double chamber pump. The benefit of a floating mass transducer driven pump for use with a hearing system is that the flow rates are low enough to cause no substantial, or only a minimal, pressure increase within the region where the hearing device is implanted. Details of illustrative embodiments are discussed below.

Figure 1:
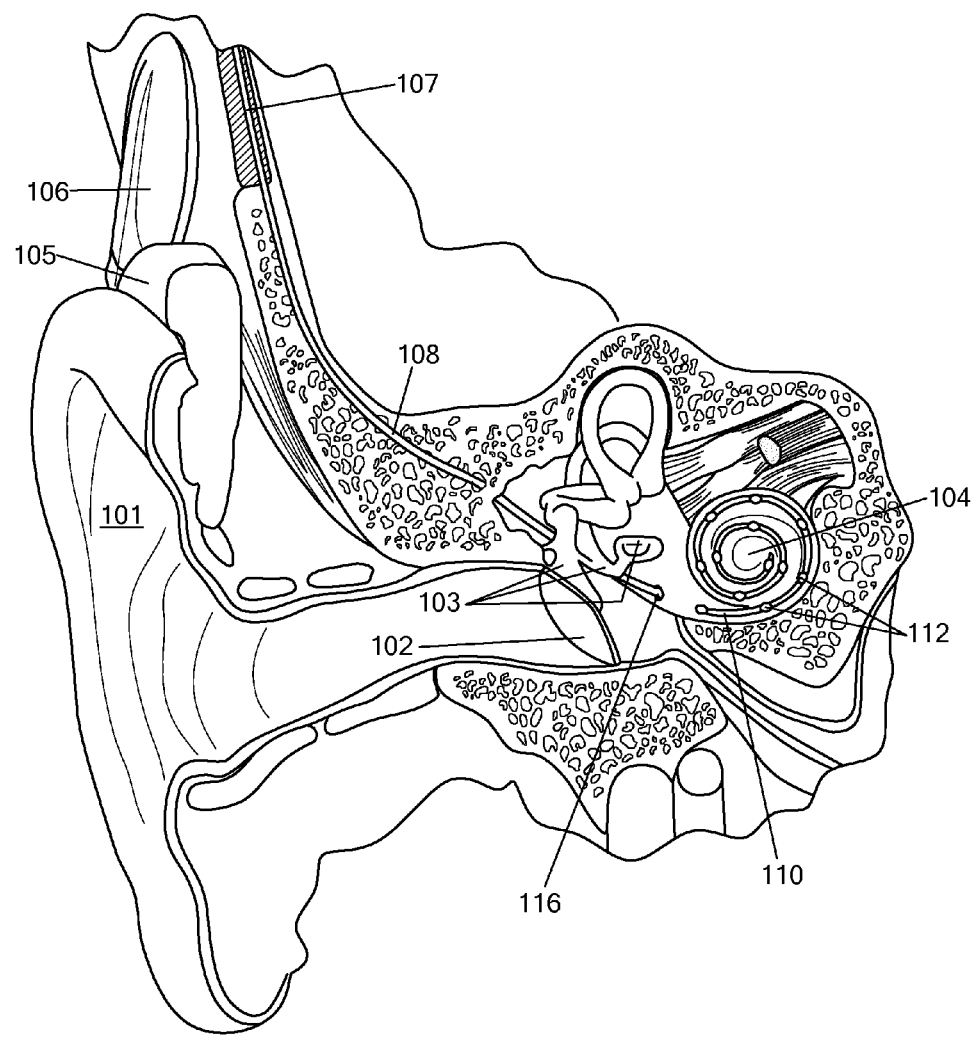
FIG. 1 schematically shows a typical human ear which includes a cochlear implant system.

FIG. 1 schematically shows the anatomy of a normal human ear. The ear typically transmits sounds, such as speech sounds, through the outer ear 101 to the tympanic membrane (eardrum) 102, which moves the bones of the middle ear 103 (malleus, incus, and stapes) that vibrate the oval window membrane of the cochlea 104. The cochlea 104 is a long narrow duct wound spirally about its axis for approximately two and three quarters turns. It includes three chambers along its length, an upper chamber known as the scala vestibuli, a middle chamber known as the scala media, and a lower chamber known as the scala tympani. The cochlea 104 forms an upright spiraling cone with a center called the modiolus where the axons of the auditory nerve reside. These axons project in one direction to the cochlear nucleus in the brainstem and they project in the other direction to the spiral ganglion cells and neural processes peripheral to the cells in the cochlea. In response to received sounds transmitted by the middle ear 103, sensory hair cells in the cochlea 104 function as transducers to convert mechanical motion and energy into electrical discharges in the auditory nerve. These discharges are conveyed to the cochlear nucleus and patterns of induced neural activity in the nucleus are then conveyed to other structures in the brain for further auditory processing and perception.

FIG. 1 also shows some components of a hearing system, such as a typical cochlear implant system, although other hearing systems may be used with embodiments of the present invention. The cochlear implant system includes an external microphone (not shown) that provides an audio signal input to an external signal processor 105 where various signal processing schemes may be implemented. The processed signal is then converted into a stimulation pattern by an external transmitter/stimulator 106, and the stimulation pattern/signal is transmitted through connected wires (not shown) to an implanted electrode carrier 107. The electrode carrier 107 has an electrode lead 108 and an electrode array 110 that is inserted into the cochlea 104 through an opening in the round window or a cochleostomy site 116. Typically, the electrode array 110 has multiple electrodes 112 on its surface that provide selective stimulation to the cochlea 104.

Hearing is impaired when there are problems in the ability to transmit sound from the external to the inner ears or problems in the transducer function within the inner ear. To improve impaired hearing, auditory prostheses have been developed. For example, when the impairment is related to the operation of the middle ear 103, a conventional hearing aid may be used to provide acoustic stimulation to the auditory system in the form of amplified sound. When the impairment is associated with the transducer function in the cochlea 104, a cochlear implant system can electrically stimulate auditory neural tissue with small currents delivered by multiple stimulation electrodes distributed along at least a part of the cochlear length. Arrays of such stimulation electrode contacts normally are inserted into the scala tympani.

Figure 2:
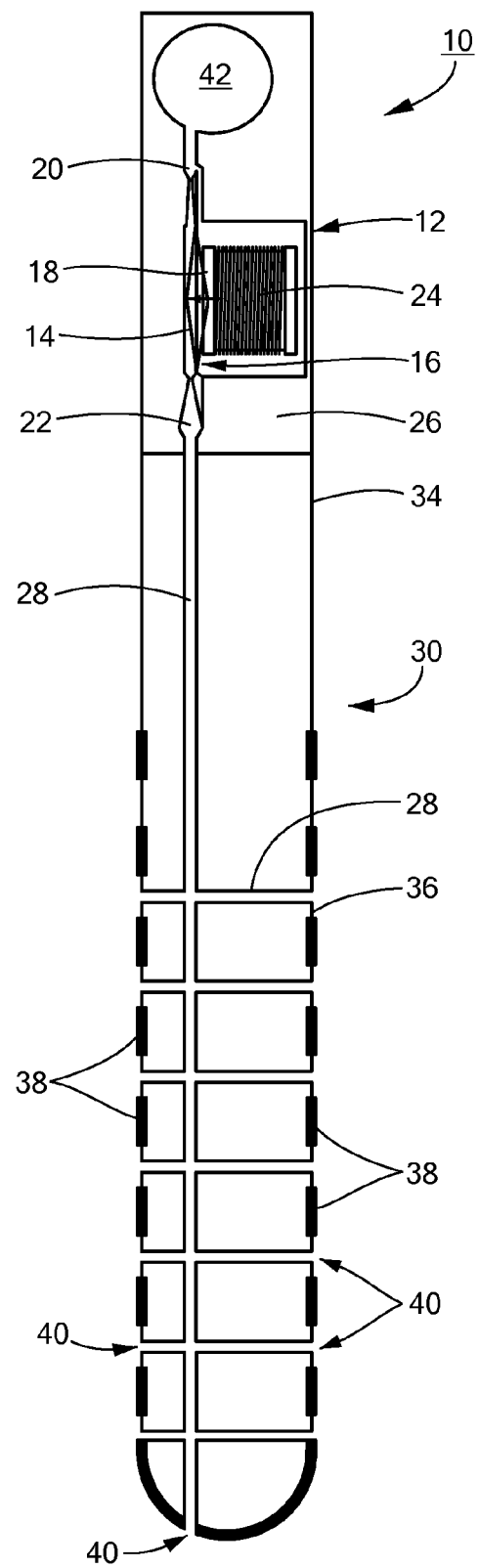
FIG. 2 schematically shows a fluid delivery system with a cochlear electrode according to embodiments of the present invention.

FIG. 2 schematically shows a fluid delivery system 10 according to embodiments of the present invention. The fluid delivery system 10 includes an implantable fluid pump 12 having a fluid chamber 14 having at least one wall 16 with a membrane 18, an inlet 20 and an outlet 22 in fluid communication with the fluid chamber 14, and a floating mass transducer 24 coupled to the membrane 18. The fluid delivery system 10 further includes an implantable hearing device having one or more fluid channels 28 in fluid communication with the fluid pump 12. The hearing device, in one embodiment, is a cochlear implant electrode 30. The electrode 30 includes an electrode lead 34 at its distal end and an electrode array 36, with stimulating electrodes 38 distributed along the array 36, at its proximal end. The electrode 30 includes one or more fluid outlets 40 in fluid communication with the one or more fluid channels 28. The fluid outlets 40 may be disposed on one side of the electrode 30, on more than one side, and/or toward the proximal end.

Figure 3A:
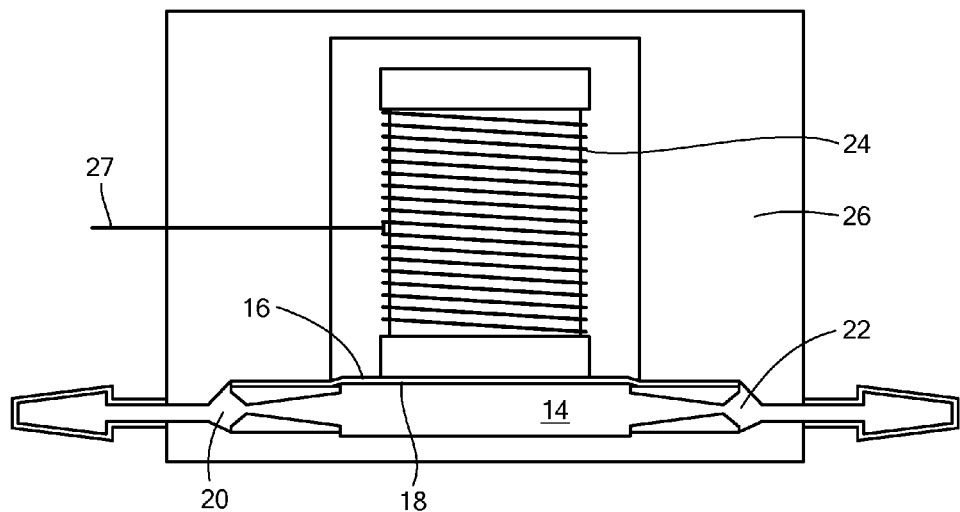
FIG. 3A schematically shows an implantable fluid pump with a floating mass transducer and FIG. 3B shows the membrane movement caused by an activated floating mass transducer according to embodiments of the present invention.
Figure 3B:
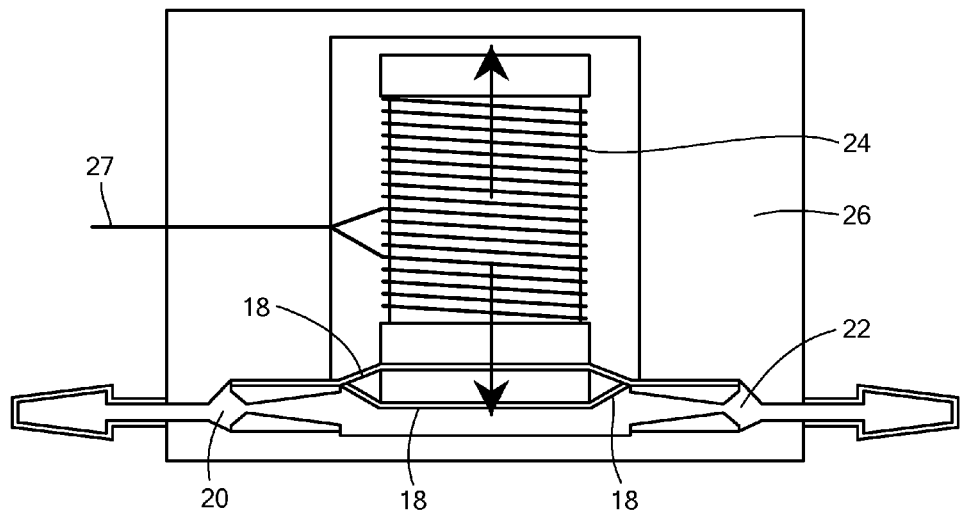

As shown in more detail in FIGS. 3A and 3B, in operation, the floating mass transducer 24 causes the membrane 18 to move when the floating mass transducer 24 is activated, e.g., up and down in the vertical direction as shown in FIG. 3B. For example, as the membrane 18 moves in a first direction (arrow pointing upward toward the floating mass transducer 24), the volume of the fluid chamber 14 is increased and fluid flows in through the inlet 20 causing the fluid chamber 14 to fill with fluid. As the membrane 18 moves in a second direction (arrow pointing downward toward the fluid chamber 14), the volume of the fluid chamber 14 is decreased, which causes the fluid to be pushed out or released from the fluid chamber 14 through the outlet 22. The floating mass transducer 24 may be disposed within a housing 26 (e.g., made of any biocompatible material such as titanium) and a lead 27 may be fed through the housing 26 in order to provide the floating mass transducer 24 with electrical power. The membrane 18 may be made of any material having sufficient flexibility (e.g., medical grade silicone) to allow the movement of the membrane 18 by the floating mass transducer 24.

The frequency of the floating mass transducer 24 and deflection of the membrane 18 defines the flow rate of the pump 12. For example, in a cochlear implant system, about 10-20 µl per day may be used for some applications. Pumping may occur continuously or in intervals, e.g., 1 minute per hour. An interval pumping mode would save energy compared to a continuous pumping mode. The implantable pump 12 is capable of delivering active agents which may not be able to be incorporated and released from the electrode 30 material itself. The release rates and intervals can be defined and adjusted depending on the particular application. Preferably, the floating mass transducer 24 may be operated from about a hertz to about a few kilohertz. Care should be taken, however, that the patient does not perceive the floating mass transducer 24 frequency due to the mechanical stimulation. For example, if a patient is deaf above 1 kHz, then the floating mass transducer 24 could be operated above that frequency. Alternatively, the floating mass transducer 24 may be operated at low hertz frequency, where the patient may not perceive the movement. A possible acoustic sensation for the patient caused by the floating mass transducer 24 can be avoided by acoustically decoupling the floating mass transducer 24 from the inner ear, which may be done by positioning and orienting it in such a way that there is minimal or no acoustic sensation in the inner ear. Appropriate designing of the microfluidic channels and structures can further reduce or erase possible acoustic sensations of the inner ear caused by the floating mass transducer 24. As known by those skilled in the art, the traveling of sound pressure waves in a fluid filled channel or tube depends on various variables. For example, a small diameter and a low Young's modulus E (modulus of elasticity) of the tube can reduce the transmission of sound pressure waves. Furthermore, additional microfluidic features or elements can be integrated in the system to further reduce or eliminate possible sound pressure waves traveling to the inner ear. For example, one or more of the channel diameters may be increased and/or a compressive/absorbent buffer may be used in the fluid chamber and/or additional chambers (with or without the buffers) may be used.

Referring again to FIG. 2, the fluid delivery system 10 may further include one or more fluid reservoirs 42 fluidly connected to the fluid pump 12. One or more of the reservoirs 42 may be implantable, e.g., coupled to and integrated with the implantable fluid pump 12, such as shown in FIG. 2, and/or one or more of the reservoirs 42 may be external and connected to the fluid pump 12 through a connecting system (not shown), such as tubes, catheters, etc. For example, the fluid pump 12 may be connected to an implantable and refillable drug delivery reservoir, such as described in U.S. Patent Publication No. 2010/0121256 by Jolly et al., hereby incorporated by reference herein in its entirety.

Figure 4:
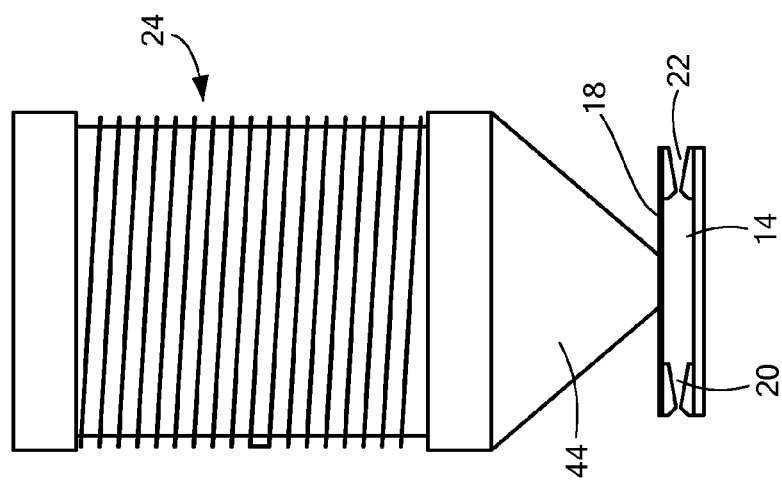
FIG. 4 schematically shows a floating mass transducer coupled to a membrane with a connecting member according to embodiments of the present invention.

The floating mass transducer 24 may be coupled to the membrane 18 in a variety of ways. For example, the floating mass transducer 24 may be integrated into the membrane 18 (such as described in more detail below in FIGS. 6A and 6B and the dual chamber configuration), may be placed directly onto the membrane 18 (such as shown in FIGS. 3A and 3B) or may be coupled to the membrane 18 by a connecting member 42 (such as shown in FIG. 4). The connecting member 42 may have any shape, e.g., a conical shape, such as shown in FIG. 4.

Figure 5:
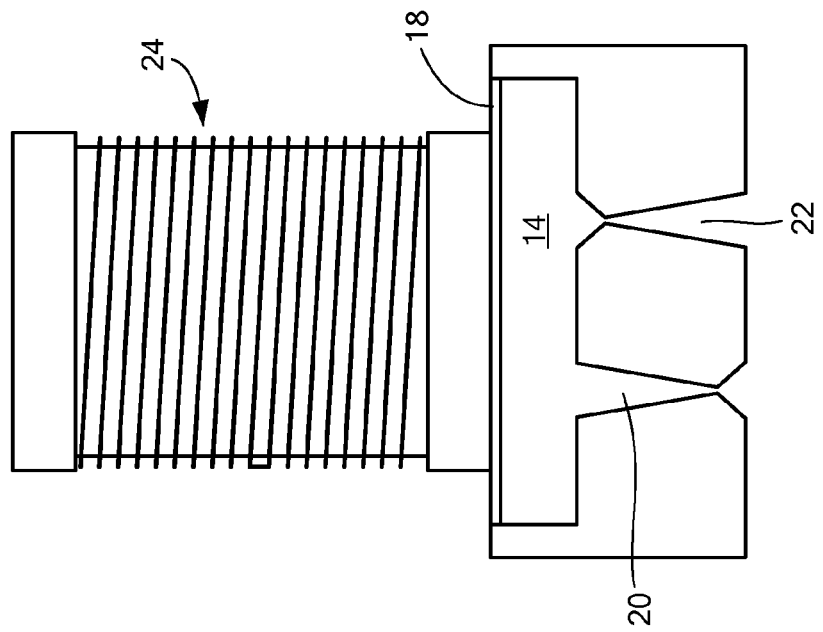
FIG. 5 schematically shows an implantable fluid pump with an inlet and outlet along the same wall according to embodiments of the present invention.

The inlet and outlets 20, 22 may be configured as valves that direct the fluid movements in the pump system. Preferably, the valves have no moving parts and use asymmetric flow resistance to direct the movements. For example, the inlet and outlets 20, 22 may be configured as diffuser/nozzle valves (such as shown in the figures) and/or Tesla valves. The inlet and outlets 20, 22 may also be check valves or any other type of valves that could be used to direct the fluid. The inlet and outlets 20, 22 may be positioned relative to the fluid chamber 14 in any configuration. For example, the inlet and outlets 20, 22 may be positioned at the sides of the fluid chamber 14 opposite to each other (such as shown in FIGS. 3A and 3B), may be positioned next to each other along the same wall (such as shown in FIG. 5), or one may be positioned at the side and one may be positioned opposite the membrane 16 (not shown).

Figure 6A:
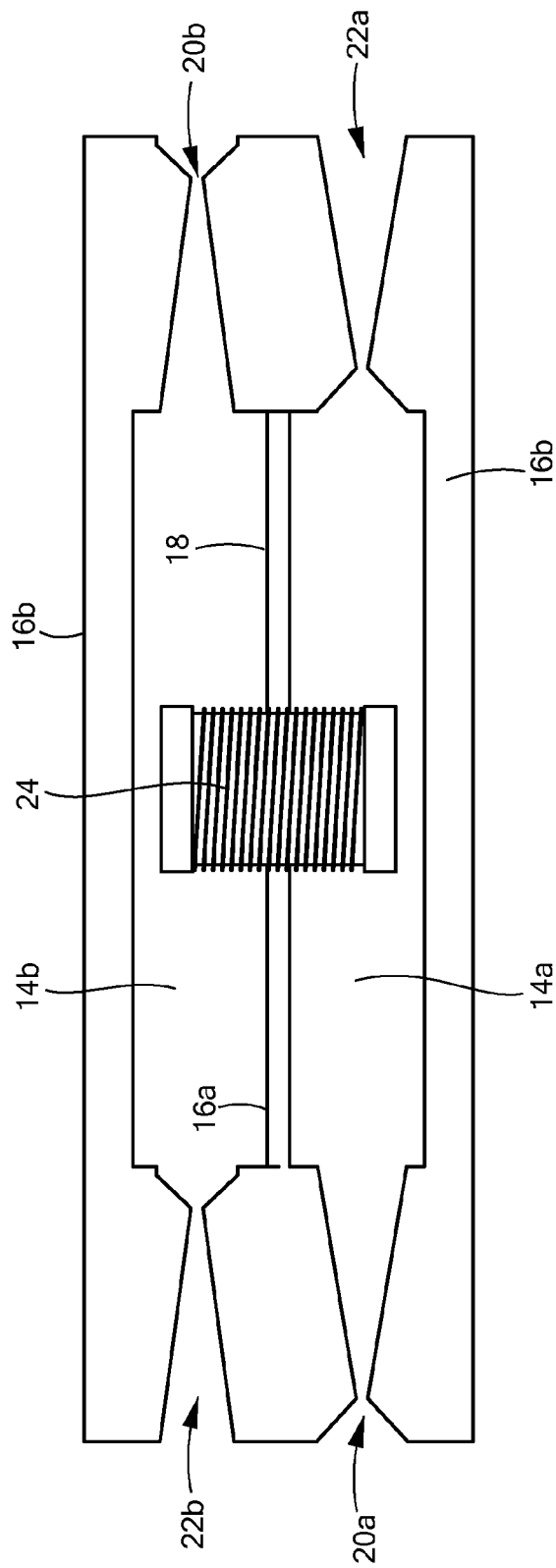
FIG. 6A schematically shows an implantable fluid pump with a double chamber system and FIG. 6B shows the membrane movement caused by an activated floating mass transducer according to embodiments of the present invention.
Figure 6B:
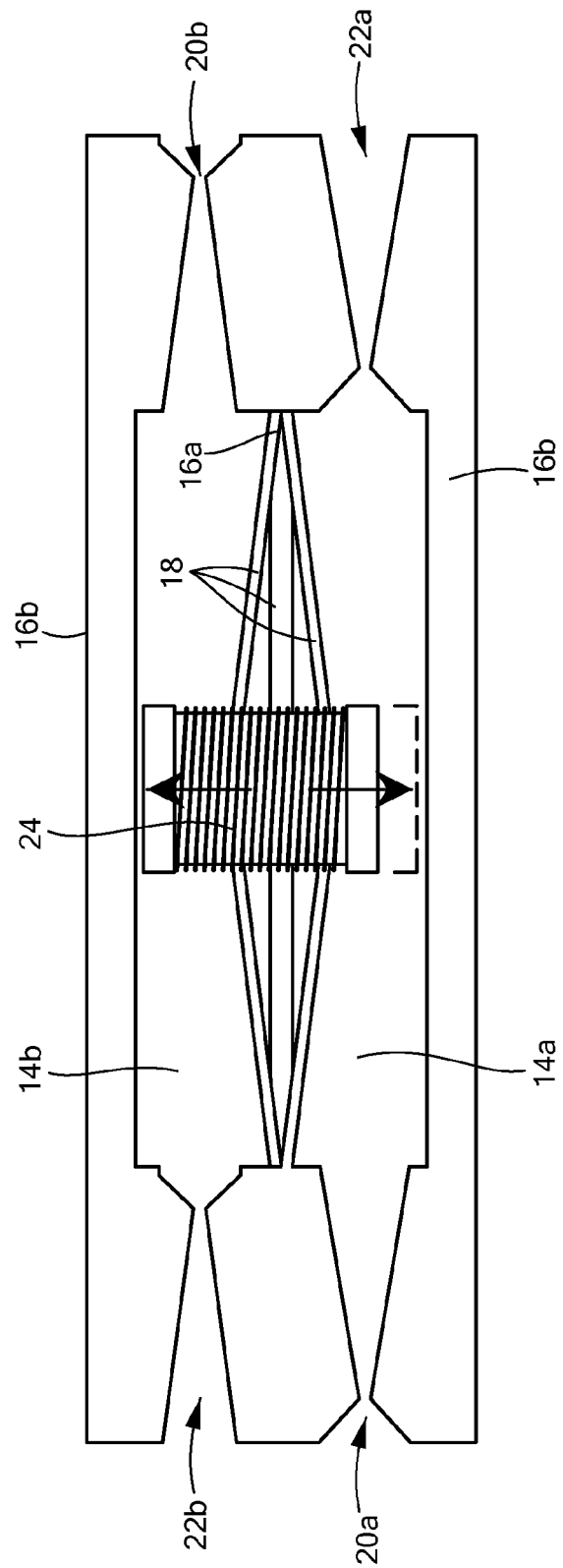

Although the fluid pump 12 has been shown as a single chamber system in FIGS. 2-5, the fluid pump 12 may have a double chamber configuration instead. For example, as shown in FIGS. 6A and 6B, the fluid chamber 14 may be divided into a first fluid chamber 14a and a second fluid chamber 14b, each of the chambers 14a, 14b, having an inlet (20a or 20b) and an outlet (22a or 22b). The first and second fluid chambers 14a, 14b are separated by an inner wall 16a of the fluid chamber 14. The inner wall 16a may include the membrane 18 (as shown in FIGS. 6A and 6B) when the floating mass transducer 24 is positioned within the fluid chamber 14, and/or an outer wall 16b of the fluid chamber 14 may include the membrane 18 when the floating mass transducer 24 is positioned outside of the fluid chamber 14 (such as shown in FIGS. 3A and 3B). When the inner wall 16a includes the membrane 18, the floating mass transducer 24 may be integrated into the membrane 18 such that a portion of the floating mass transducer 24 is positioned within each of the fluid chambers 14a, 14b (as shown in FIGS. 6A and 6B). Alternatively, the floating mass transducer 24 may be coupled to the membrane 16 and positioned on one side of the membrane 16 so that the floating mass transducer 24 is positioned within only one of the fluid chambers 14a, 14b (not shown).

Similar to the single chamber configuration, the floating mass transducer 24 causes the membrane 18 to move (e.g., up and down in the vertical direction as shown in FIG. 6B) when the floating mass transducer 24 is activated during operation. For example, as shown in FIG. 6B, as the membrane 18 moves in a first direction (arrow pointing upward), the volume of the first fluid chamber 14a is increased while the volume of the second fluid chamber 14b is decreased. As the volume is increased in the first fluid chamber 14a fluid flows in through the inlet 20a causing the fluid chamber 14a to fill with fluid. At the same time, the volume is decreased in the second fluid chamber 14b causing the fluid to be pushed out or released from the second fluid chamber 14b through outlet 22b. As the membrane 18 moves in a second direction (arrow pointing downward), the volume of the first fluid chamber 14a is decreased while the volume of the second fluid chamber 14b is increased, which causes fluid to be pushed out or released from the first fluid chamber 14a through the outlet 22a while fluid flows in to the second fluid chamber 14b through the inlet 20b.

Figure 7:
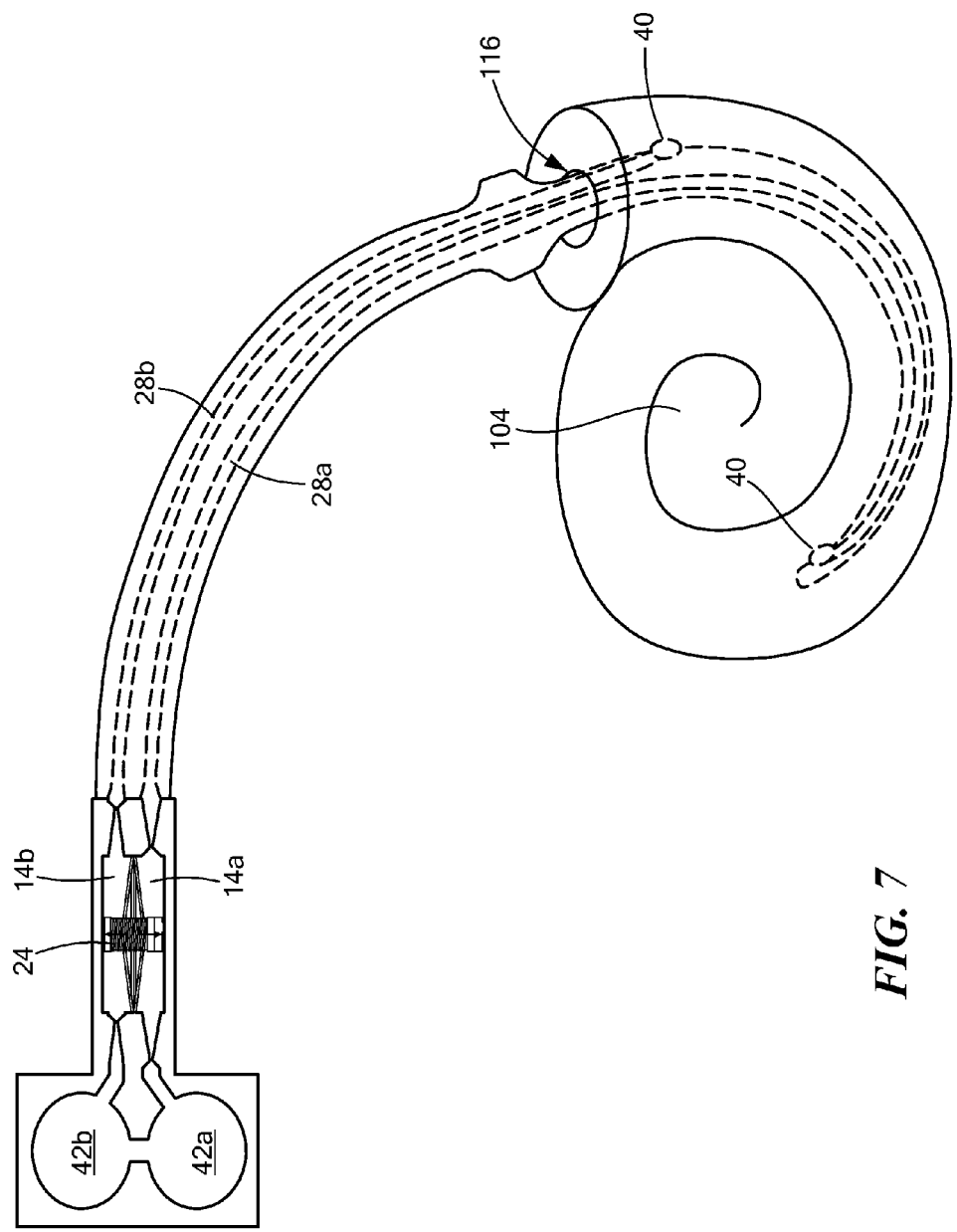
FIG. 7 schematically shows a fluid delivery system with a cochlear electrode and a double chamber pump with a circular flow pattern according to embodiments of the present invention.

The benefit of this type of double chamber pump 12 and inlet/outlet 20a, 20b, 22a, 22b configuration is that it allows for fluid flow in both directions at the same time which can provide a circular flow pattern. The circular flow pattern may allow the fluid to be circulated through the small area in which the hearing device is implanted. For example, as shown in FIG. 7, a cochlear electrode 30 may have more than one fluid channel 28 with fluid outlets 40 into the cochlear 104. The fluid, such as a drug solution, can be pumped from a first reservoir 42a into the cochlear 104 through a first fluid channel 28a, and then, through a second fluid channel 28b, the solution is taken out of the cochlear and returned to a second reservoir 42b. The first and second reservoirs 42a, 42b, may be fluidly connected so that the solution is able to flow back through to the first reservoir 42a and the process may begin again, as described above. This type of configuration may prevent a substantial increase in pressure in the inner ear due to the drug delivery. Alternatively, the first and second reservoirs 42a, 42b may not be fluidly connected, but may be connected to one or more fluid connection systems and/or one or more external reservoirs, which may or may not be fluidly connected.

Although FIGS. 6A and 6B show the two chambers 14a, 14b as having the inlets 20a, 20b on opposing sides and the outlets 22a, 20b on opposing sides of the pump 12, the inlets 20a, 20b may be along the same side and the outlets 22a, 22b may be along the other side of the pump 12. The benefit of this type of double chamber pump 12 and inlet/outlet 20a, 20b, 22a, 22b configuration is that it allows for alternating fluid flow, for example from two reservoirs 42, in order to maintain a relatively constant output of fluid into the designated area or to vary the composition or concentration of the drug dispensed into the area.

Figure 8:
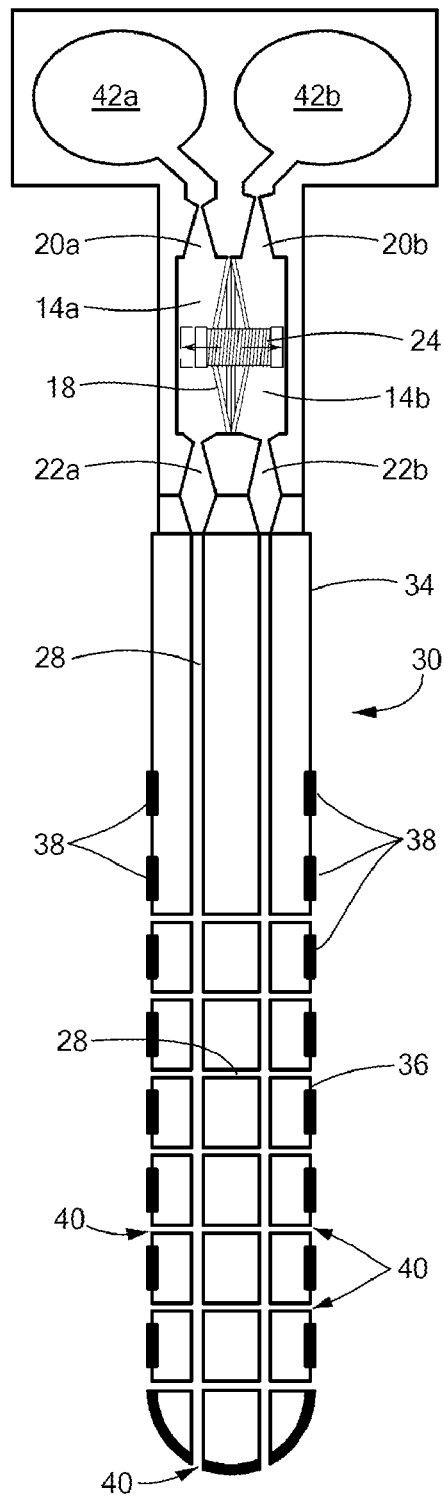
FIG. 8 schematically shows a fluid delivery system with a cochlear electrode and a double chamber pump with an alternating fluid flow pattern according to embodiments of the present invention.

For example, FIG. 8 shows a double chamber configuration in which two reservoirs 42 are fluidly connected to the double chamber pump 12. In this configuration, when the membrane 18 moves in a first direction (arrow pointing to the right towards the second fluid chamber 14b), the volume of the first fluid chamber 14a is increased while the volume of the second fluid chamber 14b is decreased. This causes fluid to flow in through the inlet 20a from the first reservoir 42a and causes fluid (which came from the second reservoir 42b) to be pushed out through the outlet 22b along the one or more fluid channels 28 and out the fluid outlets 40. As the membrane 18 moves in a second direction (arrow pointing to the left toward the first fluid chamber 14a), the volume of the first fluid chamber 14a is decreased while the volume of the second fluid chamber 14b is increased. This causes fluid to be pushed out or released from the first fluid chamber 14a through the outlet 22a, along the one or more fluid channels 28 and out the fluid outlets 40, while fluid flows in to the second fluid chamber 14b from the second reservoir 42b through the inlet 20b. The delivery of fluid through the fluid pump 12, in either the circular flow pattern or alternating fluid chamber dispensing configuration, may last the life of the hearing device depending on the reservoir configuration and/or the fluid delivery mechanism used.

Although a cochlear implant electrode 30 is discussed above with regard to the hearing device, other hearing devices may also be used with the implantable fluid pump 12. For example, a middle ear implant and/or a hearing aid may be used instead of, or in addition to, the cochlear implant or brain stem implant.

As will be appreciated by one skilled in the art, the implantable pump 12 may be used to deliver fluids with low and precise flow rates to other regions in the body, in addition to, or instead of, the inner ear. For example, other targets for local drug delivery that may be used with embodiments of the present invention include the middle ear, brain, spinal cord, neural structures in general, tumors, etc. For example, embodiments of the fluid delivery system may bring nerve growth factors to the inner ear with an appropriate delivery device which is able to delivery therapeutic agents to specific regions of the brain at low flow rates.

Although the above discussion discloses various exemplary embodiments of the invention, it should be apparent that those skilled in the art can make various modifications that will achieve some of the advantages of these embodiments without departing from the true scope of the invention. For example, although some features may be included in some embodiments and drawings and not in others, these features may be combined with any or all of the other features in accordance with embodiments of the invention as would be readily apparent to those skilled in the art based on the teachings herein.

What is claimed is:

1. An implantable fluid delivery system for use of a treatment of an ear, the system comprising:
   an implantable fluid pump comprising:
   a first fluid chamber and a second fluid chamber separated by a membrane, the membrane configured to move in a first direction increasing a volume of the first fluid chamber while decreasing a volume of the second fluid chamber, and configured to move in the second direction decreasing the volume of the first fluid chamber while increasing the volume of the second fluid chamber;
   a first inlet and a first outlet in fluid communication with the first fluid chamber;
   a second inlet and a second outlet in fluid communication with the second fluid chamber; and
   a floating mass transducer coupled to the membrane and configured to cause the membrane to move in the first and second directions;
   a first reservoir in fluid communication with the first fluid chamber;
   a second reservoir in fluid communication with the second fluid chamber; and
   an implantable hearing device having one or more fluid channels in fluid communication with the first fluid chamber and the second fluid chamber.

2. The system of claim 1, wherein the implantable hearing device includes a cochlear implant.

3. The system of claim 2, wherein the cochlear implant includes an electrode array having at least one stimulation electrode and at least one fluid outlet in fluid communication with the one or more fluid channels.

4. The system of claim 1, further comprising one or more external reservoirs in fluid communication with the first reservoir, the second reservoir, or both.

5. The system of claim 1, wherein at least one reservoir is implantable.

6. The system of claim 1, wherein at least one reservoir is coupled to the fluid pump with a fluid connecting system.

7. The system of claim 1, further comprising a connecting member that couples the floating mass transducer to the membrane.

8. The system of claim 1, wherein the first and the second reservoirs are in fluid communication with one another.

9. The system of claim 1, wherein the implantable hearing device has one or more fluid channels in fluid communication with the first fluid chamber and one or more fluid channels in fluid communication with the second fluid chamber.

10. The system of claim 1, wherein a portion of the floating mass transducer is disposed in the first chamber and in the second chamber.

11. The system of claim 1, wherein the floating mass transducer is disposed within the first chamber or the second chamber.

12. The system of claim 1, wherein the first and the second inlets and the first and the second outlets are on the same wall.

13. The system of claim 1, wherein the first and the second inlets and the first and the second outlets are on opposing walls.

14. The system of claim 1, wherein the ear is a middle ear, an inner ear, or both.

15. The system of claim 1, wherein the inner ear is a cochlea, a vestibular system, or both.

* * * * *

UNITED STATES PATENT AND TRADEMARK OFFICE
CERTIFICATE OF CORRECTION

| | |
|---|---|
| PATENT NO. | : 9,327,071 B2 |
| APPLICATION NO. | : 13/937448 |
| DATED | : May 3, 2016 |
| INVENTOR(S) | : Roland Hessler |

It is certified that error appears in the above-identified patent and that said Letters Patent is hereby corrected as shown below:

In the claims,

In Col. 8, line 60
replace "claim 1"
with --claim 14--

Signed and Sealed this
Twelfth Day of July, 2016

Michelle K. Lee
*Director of the United States Patent and Trademark Office*